United States Patent [19]

Becker et al.

[11] 4,007,008
[45] Feb. 8, 1977

[54] PREPARATION OF REFERENCE SERUM FROM ANIMAL BLOOD

[76] Inventors: Milton J. Becker, 2925 W. Jerome, Chicago, Ill. 60645; William F. Line, 829 Lathrop, River Forest, Ill. 60305

[22] Filed: July 30, 1975

[21] Appl. No.: 600,394

[52] U.S. Cl. .............................. 23/230 B; 252/408; 424/101; 195/103.5 C
[51] Int. Cl.² .................... G01N 33/16; C09K 3/00
[58] Field of Search ................. 23/230 B; 252/408; 260/112 B; 424/101

[56] References Cited

UNITED STATES PATENTS

| | | | |
|---|---|---|---|
| 3,269,911 | 8/1966 | Gibbon et al. | 424/101 |
| 3,298,789 | 1/1967 | Mast | 23/253 TP |
| 3,640,896 | 2/1972 | DeCasperis | 23/230 B X |
| 3,682,835 | 8/1972 | Louderback | 252/408 |
| 3,873,467 | 3/1975 | Hunt | 23/230 B X |

OTHER PUBLICATIONS

*Chem. Abstr.,* v. 75:71845p (1971).

Primary Examiner—Morris O. Wolk
Assistant Examiner—Timothy W. Hagan
Attorney, Agent, or Firm—McDougall, Hersh & Scott

[57] ABSTRACT

A method for treatment of animal blood to simulate human blood for use as a reference standard for automated biological testing instruments wherein the enzyme activities are reduced by base-acid treatment of the serum or plasma from animals and which may include one or more additional treatments, such as decolorizing with an oxidant, removal of inorganic phosphate with an anion exchange resin, reduction of other electrolyte levels by treatment with a mixed bed ion exchange resin, reduction of glucose by treatment with glucose oxidase and the blending of processed animal sera to achieve constituent levels corresponding with human blood serum, including lyophilization of the serum product.

27 Claims, 1 Drawing Figure

Reduction of glucose using insolubilized Glucose Oxidase on step IV of processed bovine serum Hours incubation at room temperature (22-26C.)

Glucose oxidase coupled to agarose at about 2% wt./wet wt.
100 gms. of wet wt. complex used per 1 liter of bovine serum
(equiv. of about 12 gms. glucose oxidase per 6 liters of reaction mixture).

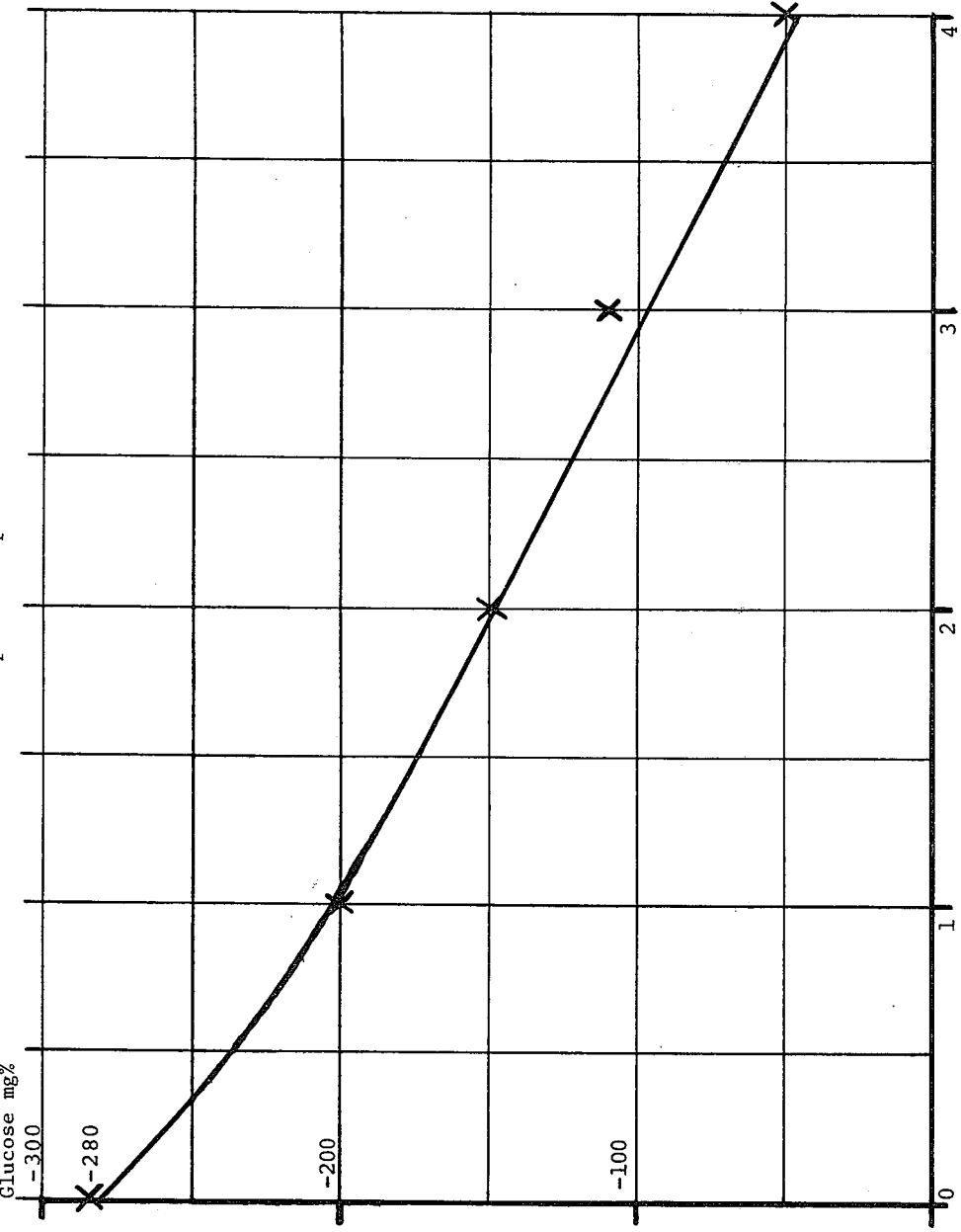
Figure 1: Reduction of glucose using insolubilized Glucose Oxidase on step IV of processed bovine serum
Glucose oxidase coupled to agarose at about 2% wt./wet wt. 100 gms. of wet wt. complex used per 1 liter of bovine serum (equiv. of about 12 gms. glucose oxidase per 6 liters of reaction mixture).

PREPARATION OF REFERENCE SERUM FROM ANIMAL BLOOD

This invention relates to a simulated human blood serum control standard and method for its preparation.

Blood serum is a complex biological fluid containing numerous components of substantial physiological importance. In the normal healthy person, the concentrations of these components fall within certain reasonably well defined limits. When one or more of these components is determined upon analysis to fall outside of these acceptable limits, various diseases or pathological conditions of the body system are indicated.

The rapid analysis of various blood serum components has become a valuable adjunct in the clinical diagnosis of disease.

In recent years, automated procedures have been developed for rapid analysis of multiple components of blood serum. Illustrative of the analytical equipment which has been made available for these purposes are the "Auto Analyzer" of Technicon, the "Robot Chemist" of Warner-Chilcott, and the "Discrete Analyzer" of Beckman Instruments. These instruments are capable of rapid and sequential determination of the concentrations of a host of blood serum components in a single blood sample. Biochemical determinations may be made, for example, with such apparatus, of the following constituents of the blood serum sample, namely, albumin, alkaline phosphatase, bilirubin, calcium, chloride, cholesterol, carbon dioxide, creatinine, glucose, lactic dehydrogenase (LDH), inorganic phosphorus, potassium, sodium, total protein, transaminases (SGOT) and (SGPT), urea nitrogen, uric acid, creatinine phosphokinase (CPK).

For construction and operation of such instruments, reference may be made to the Skeggs et al U.S. Pat. No. 3,241,432 which is capable of making simultaneously a multiplicity of different analyses of a blood serum sample with respect to the constituents referred to above and of rapidly repeating the analysis on successive samples.

In performance of the analytical tests made by the above and similar equipment on blood serum and other biological samples, it is necessary to use laboratory standard materials or so-called "reference or control standards" for purposes of calibration and control of the instrument. Accurate results in the use of these instruments, particularly in the case of multi-automated procedures, are somewhat dependent upon rapid and constant standardization of the biological determinations.

Control sera are not only employed as standards for the calibration of routine clinical chemistry determinations, particularly those that are performed on such automated equipment, but they are also employed periodically to check the performance of both the technician and the equipment.

The continued use of human plasma or serum as the raw material base for the preparation of the control standard or reference sera has several disadvantages. The cost of human blood products has escalated sharply in recent years and since there is a scarcity of human blood products, the cost will probably continue to increase.

Government regulatory agencies have recently imposed several restrictions governing the collection and marketing of human blood products. Examples of regulations passed in recent years include restriction of the anti-coagulant used in the collection of human plasma and screening the donor population for the absence of such potentially infectious materials as hepatitis associated antigen.

Thus, it is an object of this invention to produce and to provide a method for producing control sera from sources other than from human blood and which simulate human control sera for use in standardization and control of such automated instruments for analytical tests on blood serum and other biological samples; which can be prepared in a simple and efficient manner at low cost and readily available materials; which can be placed in storage over long periods of time without deterioration; which can be readily modified to represent a normal level where the constituents commonly assayed for fall within the clinically accepted normal range for human systems or modified to an elevated level wherein certain constituents, such as serum enzymes, glucose, electrolytes, etc. are elevated by human adult standards, and including several variations of such levels, and in which the standard can be made available in lyophilized form.

Toward achievement of these objectives, we have devoted considerable effort addressed to the use of non-human serum and particularly the serum of animals such as bovine, equine, porcine and the serum of sheep and the like animals, all of which are in plentiful supply and which should remain in plentiful supply at relatively low cost and with which controls can be maintained if desired in the feed lots for such animals to provide serum of relatively uniform composition from the standpoint of certain constituents.

A number of constituents in animal blood have been found to be present in concentrations which are not too different from the concentrations of the same constituents in human blood. However, differences do exist in some constituents, the more important of which are enzyme activities which are often elevated as much as 2 to 20-fold by comparison with human levels, as indicated by the following comparison of the enzyme activities in human blood with the enzyme activities in bovine serum, equine serum and porcine serum, as determined by tests performed with the Worthington-Stat-Zyme kits for enzyme assays, by kinetic data:

Table 1

| Enzymes | Enzyme Activity in International units/liter (IU/l) | | | |
|---|---|---|---|---|
| | Human Serum | Bovine Serum | Equine Serum | Porcine Serum |
| ALK-Phos (1) | 6–110 | 24–70 | 115–216 | 60–100 |
| CPK(1) | 0–70 | 60–185 | 50–188 | 2000–2500 |
| LDH(2) | 20–63 | 350–900 | 344–780 | 653–700 |
| SGPT(2) | 3–17 | 20–45 | 15–22 | 48–60 |
| SGOT(2) | 4–13 | 61 | — | — |

(1)—30° C. Reaction
(2)—25° C. Reaction

It will be seen from the above tabulation that, in almost every species, the enzyme activities in animal serum far exceed the level of corresponding enzyme activities in human blood serum, especially with respect to such enzymes as LDH, SGPT and SGOT.

Thus, in order to be able to make use of animal blood serum instead of human serum as a reference or control standard for automated or manual assays, it is important to effect reduction in such elevated enzyme activities to within the normal human range level, but without alteration in other constituent levels normally found in human blood sera.

We have succeeded in lowering enzyme activities in such animal sera without adversely affecting desirable constituents of the sera by selective denaturation of enzymes. This is accomplished by elevation of the pH of the serum with base for short periods of time, followed by neutralization with acid to normal pH.

One of the consequences of base treatment is the unfolding of protein chains disrupting the secondary and tertiary conformation of the molecules. With enzymes, such denaturation is generally accompanied by a loss in catalytic activity, which is irreversible in a majority of cases. The base treatment described herein selectively denatures clinically significant enzymes. The amount of change in enzymatic activity is dependent primarily on such controllable conditions as pH, temperature and time.

When the desired levels of enzymatic activities are reached, as determined by continuous or intermittent assay or by established procedures to monitor the reaction, the process can be stopped by neutralization of the basic reaction system with an appropriate acid to return the serum to normal blood pH levels.

Thereafter, the denatured sera can be further processed for modification of the levels of others of the constituents to simulate levels in human blood, as by treatment with glucose oxidase in the event that the glucose level is too high and/or by the addition of components to raise the levels of certain constituents, or by blending sera treated in accordance with the practice of this invention with natural sera of the same source, or other sera, or partially treated sera to provide a composition or blend having the desired composition.

Having described the basic concepts of this invention, illustration will now be made by way of a specific example applied to bovine serum, it being understood that the same treatment can be employed with the serum of other animals of the type described, by substitution of the serum of such other animals for the bovine serum in the following examples, and with the furter understanding that some of the steps may be omitted where the level of a particular constituent is either not important to the desired control standard, or originally within the level desired in the final control or reference sera product.

Assay for various of the constituents for monitoring the reaction and for procurement of the data with respect to constituents in the tabulations were conducted by methods and equipment hereinafter outlined, using the respective recommended procedures. Albumin, cholesterol, glucose and total protein assayed on an IL Clinicard; calcium and inorganic phosphorus assayed using Dow Diognostic manual kits; sodium, potassium and chloride assays with an IL analyzer; alkali phosphatase, CPK, LDH, SGOT and SGPT analyzed using Worthington-Stat-Zyme kits.

EXAMPLE 1

Preparation of Natural Bovine Serum from Bovine Blood

For the most part animal blood is derived from the slaughter of animals so that the blood represents a by-product which can be obtained in large volumes at low cost. Such slaughterhouse blood will be contaminated with hair and other entrainments. These may be removed by centrifugation and ultrafiltration.

Slaughterhouse bovine blood is collected and defibrinated to produce bovine serum as a raw material for subsequent processing. The serum is clarified by passing the raw serum through a centrifuge, such as a Sharpless centrifuge, followed by filtration, as through a millipore membrane of 1.2 to 0.45 microns. Such clarification removes most of the bacteria or spores. The resulting serum is considered to be free of microorganisms since no growth was detected after incubation on/in appropriate nutrient media. The resulting clarified serum will be referred to hereinafter and in the tables as the "original bovine serum".

EXAMPLE 2

Decolorization of Natural Serum

Frequently animal sera are hemolyzed; ie; possess a distinct red color due to contamination. Hemolysis is dependent on several factors including method of collection, manner in which a clot is allowed to form, etc. The red color may interfere with many colorimetric assays of clinical interest. Hemolyzed sera is decolorized by controlled addition of a mild oxidant. For this purpose, 20–30 milliliters of a 30% by weight $H_2O_2$ solution is added, with mixing, to 6–8 liters of serum for 10–20 minutes, at a temperature of 18°–30° C. The degree of oxidative bleaching can be monitored visually by comparison with the standard, or by way of colorimetric evaluation at about 405 nm, using a suitable colorimeter. When the desired color is reached, oxidation is stopped rather quickly by destroying the excess $H_2O_2$, as by the addition of 50–70 ml of a solution of catalase (an enzyme which converts $H_2O_2$ to $H_2O$ and $O_2$), present in a concentration of 10 milligrams per milliliter.

In the event that the inorganic phosphorus (Pi) level in the bovine or other animal sera is above the level present in human sera, or a reduction in Pi is otherwise desirable, the Pi level can be reduced effectively, preferably but not essentially before treatment to modify enzymatic activities, by addition to the animal serum of a polyamine ion exchange resin, as illustrated by the following example.

EXAMPLE 3

Adjustment of Inorganic Phosphorus Level in Serum

200–300 grams of ion exchange resin of the polyamine type (IR-4B or CG-4B of Rohm and Haas) of 200–400 mesh, in chloride form, is added with stirring to 6–8 liters of serum at 18°–30° C and mixing is continued until the reduction of inorganic phosphorus to the desired level is attained, as determined by intermittent assay. At this point, the polyamine ion exchange resin (IR-4B or CG-4B) is separated from the serum as by filtration or centrifugation.

EXAMPLE 4

Reduction in Enzymatic Activities

Elevated levels of enzyme activities are adjusted downward, in accordance with an important concept of this invention, by the addition of a strong base, in amounts to raise the pH to above neutrality and preferably to within a range of 10.5±1. Representative of the inorganic bases that can be used are the alkali metal hydroxides, such as lithium, sodium, potassium, and ammonium hydroxides, and representative of the strong organic bases that can be used are tetramethyl ammonium hydroxide, tetraethyl ammonium hydroxide, and other quaternary ammonium salts. The pH is maintained at a level above neutrality and the temperature of the serum is maintained within the range of 2°–30° C until the enzymatic activities are reduced to desired levels. Continued reduction in enzymatic activities is terminated by return of the pH to normal blood pH, by neutralization with a strong acid such as $H_2SO_4$, HCl and the like inorganic acids. In this example, use is made of an aqueous solution of 6 N NaOH, added in amounts to raise the pH to 10.5±1. The progress of enzyme denaturation was determined by intermittent assay. After about 15–30 minutes, with continuous stirring, the desired levels of enzymatic activities were attained (see Table 2), and the reaction was terminated by neutralization to pH 7.5 to 7.7 with 6 N HCl.

The selection of bases for denaturation of the enzyme and the selection of acid for neutralization will depend somewhat on the subsequent processing of the treated serum, the composition of the product desired and the non-interference of the added base or acid.

The following is a tabulation of the analysis of natural human blood serum as compared to bovine blood serum subjected to the processing of Examples 1 to 4 with the analysis of indicated changes in composition as the result of each such treatment.

the lower portion of the range for normal human serum.

Animal blood frequently has potassium ion levels higher and as much as two times higher than in human blood. When, as indicated in the above tabulation, the ion levels exceed a level of normal human serum, the ion concentrations can be reduced by contact with an ion exchange medium such as an ion exchange resin. Ions such as chloride, potassium, and/or sodium may be further increased above that in the original serum during the base-acid treatment, as described in Example 4. With reference to the above tabulation, it will be seen that both the chloride and sodium ion concentrations are increased during base-acid treatment.

The concentration of ions can also be controlled to maintain certain levels by control of the herd in the feed lot but it is far simpler and less expensive to provide for adjustment of the ion concentration by ion exchange.

EXAMPLE 5

Removal of Excess Ions

500–600 grams of 20–50 mesh ion exchange, mixed bed resin of the $OH^-$ and $H^+$ forms (Amberlite MB-1) is stirred into 6–8 liters of serum from Example 4, at a temperature of 8°–30° C until the desired ion reduction Table 2

| Constituent | Normal Human range values | Assay values of constituents after processing bovine blood in accordance with Examples 1 to 5 | | | | |
|---|---|---|---|---|---|---|
| | | Ex. 1 Original | Ex. 2 Decolorizing | Ex. 3 Pi reduction | Ex. 4 Base-Acid | Ex. 5 |
| Albumin | 3.4–5.5 g% | 3.58 | 3.75 | 3.80 | 3.70 | 3.54 |
| Alk. phos. | 6–110 IU/l | 67 | 72.2 | 65.2 | 30.1 | 27.4 |
| Calcium | 8.5–11.4 mg% | 9.0 | 8.5 | 8.4 | 7.8 | 1.2 |
| Chloride | 98–109 meq./l | 101 | 99 | 118 | 172 | 104 |
| Cholesterol | 110–340 mg% | 133 | 123 | 125 | 138 | 136 |
| CPK | 0–70 IU/l | 79 | 52.5 | 55 | 2.5 | 1.88 |
| Glucose | 70–120 mg% | 244 | 230 | 228 | 225 | 230 |
| Pi | 2.5–4.8 mg% | 8.1 | 7.91 | 3.95 | 4.55 | 0.85 |
| LDH | 20–63 IU/l | 394 | 380 | 370 | 10 | 8.5 |
| K | 3.6–5.5 meq./l | 7.8 | 7.7 | 7.4 | 7.5 | 3.52 |
| Na | 135–148 | 145 | 143 | 142 | 195 | 136 |
| SGOT | 4–13 IU/l | 61.2 | 57.2 | 50 | 3.6 | 4.0 |
| SGPT | 3–17 " | 22.1 | 19.5 | 18.2 | 2.1 | 1.8 |
| Tot. protein | 6–8.2g% | 7.25 | 7.15 | 7.45 | 6.46 | 6.87 |

It will be seen that by comparison with normal human blood, the original bovine serum is within the range of human serum except for the CPK, LDH, SGOT and SGPT, and above the range for inorganic phosphorus, glucose and potassium.

As expected, very little change in constituent levels occurs as the result of the decolorizing treatment of Example 2.

Treatment to reduce inorganic phosphorus, in accordance with Example 3, affects only the Pi value by reducing the amount of Pi from 8.1 mg per 100 cc to 3.95 mg per 100 cc, which is well within the normal human range values. The treatment to reduce Pi does increase the concentration of chloride ions to a level above the normal human range values but this can be easily compensated by a subsequent ion exchange for adjustment of inorganic ions, as will hereinafter be described.

The denaturation of the enzyme activities by the base-acid treatment, represented by Example 4, is quite notable. CPK is reduced from 55 to a low level of 2.5 international units per liter (IU/l), LDH is reduced from 370 to 10 IU/l; SGOT is reduced from 50 to 3.6 IU/l, and SGPT is reduced from 18.2 IU/l to 2.1, all in ($Na^+$, $K^+$, $CL^-$) is achieved. The ion exchange resin is then removed from the serum, as by filtration or by centrifugation. The results of the treatment in accordance with Example 5 are tabulated in Table 2.

As shown in the foregoing tabulation, the amount of glucose in bovine or other animal serum may be at a level higher than that in normal human serum. In such instance, it is desirable to effect a reduction in the amount of glucose to a level within the normal human range, as illustrated by the following example.

EXAMPLE 6

Reduction of Glucose

Reduction in glucose level can be accomplished, either prior to or after reduction of enzymatic activities, in accordance with the practice of this invention, by oxidation with an enzyme which converts the glucose to gluconic acid without undesirable effect on others of the constituents of the serum.

To 6–8 liters of serum, such as the product of Example 5, addition is made of 12 grams of glucose oxidase supported on an insoluble matrix. The reaction is allowed to proceed with mixing at a temperature of 18°–30° C until the glucose is reduced to the desired level, as indicated by continuous or intermittent assay. The reaction is stopped by removal of the glucose oxidase from the serum, as by filtration or centrifugation. FIG. 1 is a curve showing the reduction in glucose versus time, using glucose oxidase on an insoluble support in accordance with Example 6.

Sera processed in accordance with the various examples, representative of the practice of this invention, may now be adjusted as to the various constituents in a number of ways.

When, for example, it is desired to raise the level of enzymatic activities to between the level of the original serum and that resulting from treatments in accordance with Example 4, the serum from Examples 4, 5 or 6 can be blended back with original serum from Example 1 to strike a desired level between their respective enzymatic activities, depending upon the amount of one blended with the other. Such blending allows for a minimal amount of added extrinsic enzyme.

Instead of blending as above, or in combination therewith, specific enzymes or other constituents may merely be added to the sera processed in accordance with the practice of this invention, to arrive at enzyme activities or concentration of constituents desired in the final product.

Still further, sera from different animals will have different concentration of constituents and activities whereby sera from different animals may be processed in accordance with the practice of this invention to effect reduction in enzymatic activity levels and others of the constituents described, and then blended at various stages of the process to yield a composite in which levels of the various constituents may be adjusted, thereby to provide flexibility in arriving at the final product for lyophilization or use.

By way of example, 9 parts by volume of the product of Example 4, when blended with one part by volume of original serum of Example 1, yields a reformulated serum having enzymatic activities equivalent to normal human range values as illustrated by the following table.

by the addition of albumin which is a rather expensive material.

Animal blood can be supplied from various sources and the original levels of the various constituents will depend somewhat upon such factors as physiology, metabolic rate, diet genetics, and forced adaptation to the environment. As a result, it is the usual practice to assay the lot of serum to categorize the serum before processing for adjustment of constituent levels in accordance with the practice of this invention.

As pointed out in example 1, for the most part, animal blood is derived from the slaughter of animals so that the blood represents a by-product which can be obtained in large volumes at low cost. Such slaughterhouse blood will often be contaminated with hair and other entrainments. Such undesirables can be removed by ultrafiltration, but it is preferred to effect such removal in conjunction with defibrination of the blood to produce the natural serum. For more complete defibrination, the whole blood is held in a cold room overnight to allow the particulate material and fibrinogens to settle out. Thereafter it is centrifuged to remove the particulate matter and provide a clarified serum which is supplied for the process in accordance with the practice of this invention.

Adjustment of enzymatic activities by base-acid treatment is primarily a time — pH relationship. When, for example, the pH is raised above 11.5, the effect is so rapid that almost all of the enzymatic activities are destroyed before an assay can be made to determine their levels. Thus it is desirable to make use of a pH level, above normal serum pH, which gives ample time for assay to determine the levels of enzymatic activities for monitoring during the denaturing process. The preferred pH range for denaturation is about 10.5 ± 1. Temperature is not overly critical but it is undesirable to exceed ambient temperature and it is preferred to carry out the base-acid reaction within the range of 2°–30° C.

This procedure for inactivation of enzymatic activity has minimum effect on other constituents assayed, such as albumins and globulins, lipid, cholesterol, glucose, Table 3

Example of blending/reformulation of processed borine serum to yield enzyme activities equiva-

| Enzyme | Normal Human Range Values IU/l | Step I | IV IU/l | Blend of I:IV (1 vol: 9 vol.) IU/l | (1)* | (2)** |
| --- | --- | --- | --- | --- | --- | --- |
| Alk. phos. | 6–110 | 67 | 30 | 33.7 | 67.9 | 56.1 |
| CPK | 0–70 | 79 | 2.5 | 10 | 82.5 | 52.3 |
| LDH | 20–63 | 394 | 10 | 49 | 49 | 39.4 |
| SGOT | 4–13 | 61 | 3.6 | 9.2 | 15.2 | 10.6 |
| SGPT | 3–17 | 22 | 2.1 | 4.0 | 20.4 | 15.8 |

*(1)Reformulated blend to add extrinsic enzymes where needed to compensate for losses as a result of lyophilization to which the reformulated serum is subsequently subjected
**(2)Reformulated blend after lyophilization The blended serum as well as the serum produced in accordance with the practice of this invention can be lyophilized by conventional lyophilization procedures well known to the skilled in the art. Usually, lyophilization will result in a loss of the order of 10–30% of enzymatic activities as indicated in Table 3.

The invention is designed to effect the desired adjustment in constituent levels without excessive dilution of constituents, such as albumin and total protein in the serum, otherwise such dilution will have to be made up and the like, but is specific mostly for the enzymes.

As described in Example 4, use can be made of strong bases such as KOH, NaOH, LiOH, quaternary ammonium compounds such as tetraethyl or tetramethyl ammonium hydroxide and the like, and strong acids such as HCl, $H_2SO_4$ and other inorganic acids for neutralization. It is preferred to make use of concentrated solution of such bases and acids to minimize change in volume.

Neutralization by acid to original serum pH levels of 7.4 to 7.8 operates automatically to stop further denaturation.

The various process steps are monitored by continuous or intermittent assay to determine when the reaction should be stopped to achieve the desired constituent levels sought to be obtained by the particular processing step. Thus it is desirable to moderate the reaction rate so that control by monitoring assays can be maintained.

It will be understood that changes may be made in the details of formulation and operation without departing from the spirit of the invention, especially as defined in the following claims.

We claim:

1. A method for reducing enzyme activities in animal serum or plasma comprising the steps of raising the pH of the serum or plasma to a level above normal serum pH by the addition with mixing of a base, and then terminating the reaction for reduction of enzyme activities by neutralizing the serum or plasma with an acidic medium.

2. The method as claimed in claim 1 in which the base is selected from the group consisting of an alkali metal hydroxide, ammonium hydroxide, and quaternary ammonium salts.

3. The method as claimed in claim 2 in which the quaternary ammonium salt is selected from the group consisting of tetraethyl ammonium hydroxide and tetramethyl ammonium hydroxide.

4. The method as claimed in claim 1 in which the base is added as a concentrated solution to minimize dilution of the serum or plasma.

5. The method as claimed in claim 1 in which the base is added in an amount to raise the pH of the serum to a level which does not exceed 11.5.

6. The method as claimed in claim 1 in which the base is added in an amount to raise the serum to a pH of 10.5 ± 1.

7. The method as claimed in claim 1 in which the reaction is carried out at a temperature within the range of 2°–30° C.

8. The method as claimed in claim 1 in which the acidic medium is a strong acid.

9. The method as claimed in claim 8 in which the acid is selected from the group consisting of $H_2SO_4$ and HCl.

10. The method as claimed in claim 1 in which the serum or plasma is derived from an animal selected from the group consisting of bovine, equine, porcine, sheep, human, and mixtures thereof.

11. The method as claimed in claim 1 which includes the step of decolorizing hemolyzed serum by treatment with a mild oxidant.

12. In the preparation of an animal serum which simulates human serum from the standpoint of constituents for use as a control standard with automated biological test equipment, the steps of reducing the enzymatic activities in the animal serum to levels corresponding to that in human serum by adding a concentrated basic material to the animal serum with stirring to raise the serum to a pH level above neutrality, monitoring the mixture to determine the reductions in enzyme activities, and then neutralizing the mixture with an acidic medium when the desired reduction in enzyme activities has been achieved.

13. In the method as claimed in claim 12 in which the basic material is added an amount to raise the pH of the serum to a level above normal serum pH but to a level which does not exceed a pH of 11.5.

14. In the method as claimed in claim 12 in which the serum is adjusted by the basic material to a pH of 10.5 ± 1.

15. In the method as claimed in claim 12 in which the basic material is selected from the materials consisting of an inorganic base selected from the group consisting of an alkali metal and ammonium hydroxide, and an organic base selected from the group consisting of a quaternary ammonium salts, tetraethyl ammonium hydroxide and tetramethyl ammonium hydroxide.

16. In the method as claimed in claim 12 in which neutralization is effected by the addition of a strong acid in an amount to reduce the pH of the serum to within the range of normal serum pH.

17. In the method as claimed in claim 12 in which the reaction is carried out at a temperature within the range of 2°–30° C.

18. In the method as claimed in claim 12 in which the basic material and acidic material are added in concentrated solution to minimize dilution of the serum.

19. In the method as claimed in claim 12, the inclusion of the step of decolorizing the serum when the serum is a hemolyzed serum by mixing a mild oxidant with the serum at a temperature within the range of 18°–30° C.

20. In the method as claimed in claim 19 in which the mild oxidant is $H_2O_2$ and in which the oxidizing agent is destroyed by adding catalase.

21. In the method as claimed in claim 12 which includes the step of reducing inorganic phosphorus in the serum by contacting the serum with an ion exchange resin, and then removing the ion exchange resin when the inorganic phosphorus has been reduced to the desired level.

22. The method as claimed in claim 12, which includes the step after base-acid treatment of the serum to reduce enzyme activities, of removing excess ions from the serum by contacting the serum with an ion exchange medium until the desired level of ion concentration is achieved, and then removing the ion exchange medium from the serum to prevent further ion removal.

23. The method as claimed in claim 22 in which the ion exchange medium is a mixture of ion exchange resins of the $OH^-$ and $H^+$ form.

24. The method as claimed in claim 12 which includes the step of reducing glucose in the serum by mixing glucose oxidase with the serum while maintaining the temperature below 30° C until the glucose in the serum is reduced to the desired level, and then separating the glucose oxidase from the serum to terminate further reduction of glucose beyond the desired level.

25. In the method as claimed in claim 12, the inclusion of the step of lyophilizing the final product.

26. A lyophilized product produced by the method of claim 25.

27. In the method as claimed in claim 12, in which the serum is blended with other serum having different constituent levels to yield a blend having the desired enzyme level.

* * * * *